United States Patent [19]

Shinpo

[11] Patent Number: 4,822,612

[45] Date of Patent: Apr. 18, 1989

[54] ANTICANCER AGENT

[75] Inventor: Kunihiro Shinpo, Nagareyama, Japan

[73] Assignee: Chlorella Industry Co., Ltd., Tokyo, Japan

[21] Appl. No.: 882,301

[22] Filed: Jul. 7, 1986

[30] Foreign Application Priority Data

Jul. 16, 1985 [JP] Japan ................... 60-156517

[51] Int. Cl.$^4$ .................. A61K 35/80; A61K 37/10
[52] U.S. Cl. ......................... 424/195.1; 514/8
[58] Field of Search ................. 424/195.1; 514/8

[56] References Cited

FOREIGN PATENT DOCUMENTS

| 0049632 | 4/1982 | European Pat. Off. |
|---|---|---|
| 56-18923 | 2/1981 | Japan . |
| 57-32224 | 2/1982 | Japan . |
| 58-128322 | 7/1983 | Japan . |
| 61-69728 | 4/1984 | Japan . |

Primary Examiner—John W. Rollins
Attorney, Agent, or Firm—Bacon & Thomas

[57] ABSTRACT

An anticancer agent extracted and isolated from chlorella is disclosed. This anticancer agent is a kind of glycoprotein having an average molecular weight of $4.5 \times 10^4$, of which protein moiety consists of $\alpha$-helix and random coil, sugar moiety consists of $\beta$-polysaccharide, and circulor dichroism spectrum has a positive peak at 275 nm.

5 Claims, 2 Drawing Sheets

ANTICANCER AGENT

BACKGROUND OF THE INVENTION (a) Field of the Invention

This invention relates to an anticancer agent extracted and purified from a micro green alga, Chlorella.

(b) Description of the Prior Art

The present applicant has already proposed a cancerocidal substance which is consisted of a glycoprotein component having a cancerocidal effect and extracted from Chlorella, a micro green alga, which glycoprotein has a molecular weight of 121,000 isoelectric point of pH8.6, sugar-protein ratio of 1:1 and content of helix region of 19%. [Japanese patent disclosure (Kokai) No. 58-128322].

Although this glycoprotein has a definite cancerocidal effect, there has been a strong demand to search for an anticancer agent having a higher cancerocidal effect.

SUMMARY OF THE INVENTION

The object of the present invention is to extract and isolate a substance having a stronger cancerocidal effect from Chlorella.

To accomplish the object, the present inventor intensively studied the series of the above glycoprotein component to find an anticancer agent having stronger anticancer effect that the above glycoprotein.

The present inventor has found as a result that a substance extracted from Chlorella, a micro green alga, which has a molecular weight of $4.5 \times 10^4$ of which protein moiety consists of $\alpha$-helix and random coil, sugar moiety consists of $\beta$-polysaccharide, and circular dichroism spectrum has a positive peak at 275 nm, has a stronger cancerocidal effect.

DESCRIPTION OF THE PREFERRED EMBODIMENT

Figure 1:
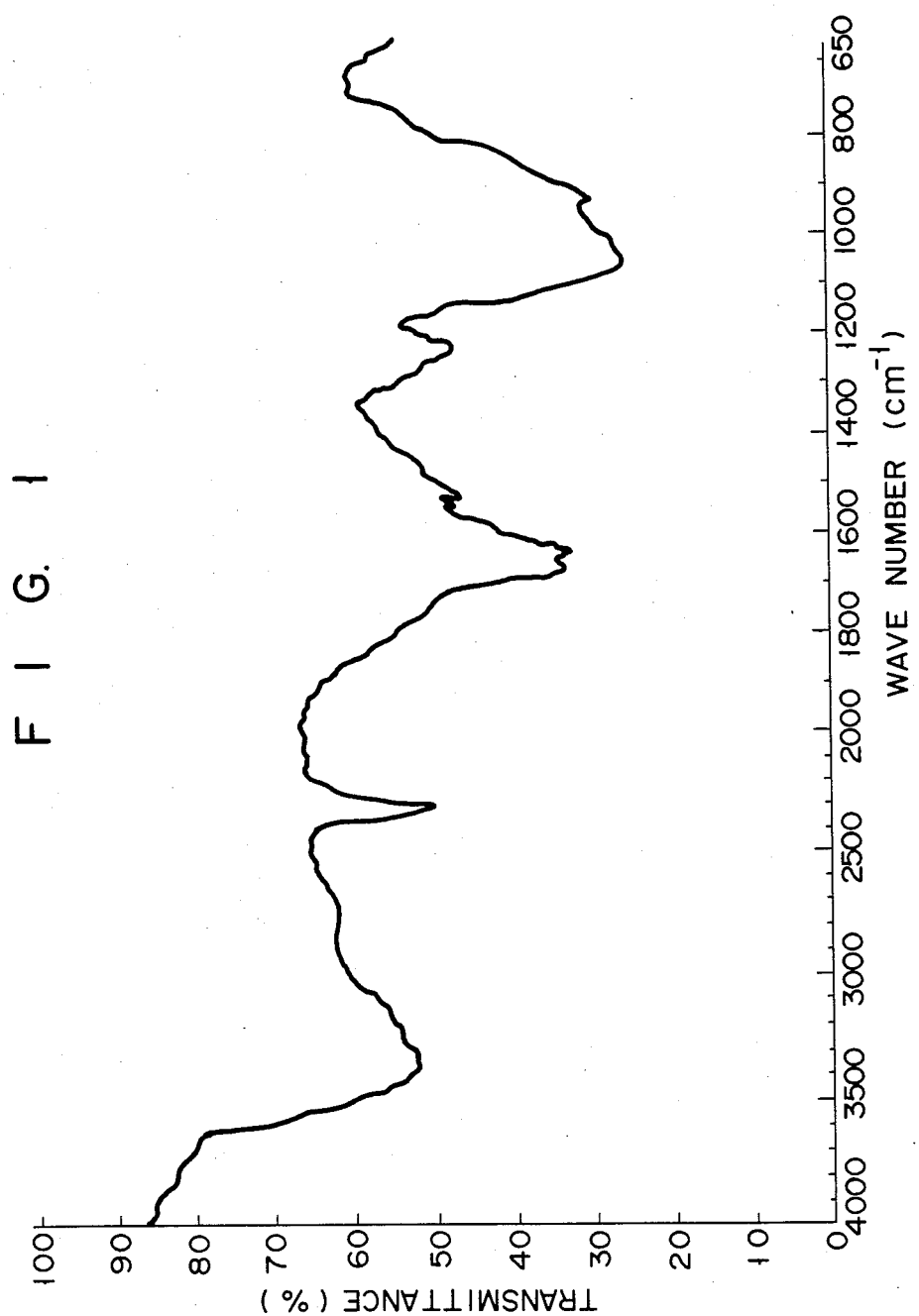
FIG. 1 shows a spectrum obtained by subjecting the anticancer substance of the present invention to an infrared spectroscopic analysis.

An example of isolating the substance of the present invention from Chlorella will now be described.

Isolation of anticancer agent from Chlorella

First, a raw cake of Chlorella cultured by using carbon dioxide gas, acetic acid, glucose or the like as the carbon source was prepared. Alternatively, a Chlorella body (powder) was prepared by spray-drying or by lyophilizing the raw cake of Chlorella.

Thereafter, 500 g of Chlorella body (or 5 liters of Chlorella raw cake) was dispersed in 5 liters of water and was extracted with hot water at 95° to 100° C. for 20 to 30 minutes. The mixture was then centrifuged at 3,000 to 10,000 rpm for 20 to 30 minutes, and the supernatant was collected as the hot water extract of Chlorella. The solvent utilized in this extraction step is not restricted to water, and aqueous dilute acid and aqueous dilute base may also be used without raising any problem. The weight of the hot water extract thus obtained was 75 g (in terms of powder).

Then the hot water extract was concentrated under reduced pressure at a temperature of 50° C. and then distilled water was added to the concentrate to obtain 1 liter of an aqueous mixture.

This mixture was subjected to an ultrafiltration and was divided into two fractions, that is, a high molecular fraction which did not pass through the ultrafilter (hereinafter referred to as fraction A) and a low molecular fraction which passed through the ultrafilter (hereinafter referred to as fraction B). The yields of the fractions A and B were 45 g and 30 g, respectively (both weights are in terms of powder).

Then 3 liters of water was added to 4.5 g of fraction A and the pH was adjusted to 5.5. To this, 0.2 g of $\alpha$-amylase in 1 liter of phosphate buffer saline was added. The mixture was incubated at 37° C. for 24 hours in an incubator to hydrolyze the fraction A. Thereafter, $\alpha$-amylase was deactivated by heating the mixture at 80° C. The whole mixture was dialized and the hydrolyzed sugar was decanted, and the remnant was dried under reduced pressure. The yield of the hydrolysate of fraction A was 30 g.

The the hydrolysate of fraction A thus obtained was subjected to gel filtration using a column (20 cm in inner diameter; 1.5 m in length) containing Bio-gel P-100 (tradename of Bil Rad Laboratories Inc.). The sample was developed with water, and a fraction showing the largest optical density at 280 nm was collected. The fraction thus collected was dried under reduced pressure while cooling with water to obtain the desired glycoprotein. The yield of the glycoprotein was 5 g (in terms of powder), so that the percentage yield with respect to Chlorell body (500 g) was 1%.

The properties of the thus obtained glycoprotein are now listed below.

(i) Molecular weight

① Average molecular weight determined by electrophoresis: phoresis:

$4.5 \times 10^4$

② Average molecular weight determined by using an analytical ultracentrifuge (manufactured by Hitachi, Ltd.: absorption scanning recorder 282-0060 type):

$4.5 \times 10^4$ (ii) Purity

It was proved that the obtained glycoprotein was pure by

① gel filtration

② sedimentation pattern in analytical untracentrifugation, and

③ electrophoresis in SDS (sodium dodecyl sulfate) polycrylamide gel.

(iii) Infrared Spectroscopic Analysis

A crystal of the glycoprotein was examined using an infrared spectroscopic analyzer (manufactured by Hitachi, Ltd.: Model 260-10 type) ($IR\alpha_{max}^{KBr} \cdot cm^{-1}$), the spectrum shown in FIG. 1 was obtained.

① An absorption peak is observed at 3,300 to 3,400 $cm^{-1}$ which shows the mixture of $\gamma_{O-H}$ of hydroxyl group and $\gamma_{N-H}$ of peptide bond, which is characteristic to glycoperotein.

② Absorption peaks are observed at 1,670 and 1,560 $cm^{-1}$ showing amide I band and amide II band, respectively, which show the existence of $\alpha$-helix.

③ Absorption peaks are observed at 1,645 and 1,540 $cm^{-1}$ showing amide I band and amide II band, respectively, which show the existence of random coil.

④ Since the absorption intensities of the bands showing the $\alpha$-helix and random coil are substantially identical, the contents of $\alpha$-helix and random coil are substantially identical, so that the content ratio thereof is 1:1.

⑤ Amide III band of the two structure is observed at 1,300 cm$^{-1}$, which is inherently weak.

⑥ At 1,230 cm$^{-1}$ and at 1,100 to 1,000 cm$^{-1}$ (finger print region), there is shown a stretching vibration of carbon-hydroxyl group of the polysaccharide, the maximum intensity thereof being at about 1,050 cm.$^{-1}$.

⑦ The absorption peak at 930 to 905 cm$^{-1}$ shows the β-bond of the polysaccharide. The absorption at 930 cm$^{-1}$ shows the asymmetric stretching vibration of carbon-oxygen-carbon of a pyranose ring.

⑧ The absence of the absorption peak at 840 cm$^{-1}$ shows the absence of α-polysaccharide.

By the analysis as stated above 1 to 8, it is confirmed that the substance is a glycoprotein, that the protein moeity thereof consists of α-helix and random coil, and that the sugar moiety thereof consists of β-polysaccharide.

(iv) Circular Dichroism spectrum (CD curve)

Ten mg of the substance was dissolved in 20 ml of distilled water and the solution was analyzed for its circular dichroism spectrum using an optical rotatory dispersion spectrophotometer (manufactured by Hitachi, Ltd.: UV-5 type) (CD solution of pH7.0) to obtain a spectrum shown in FIG. 2.

Figure 2:
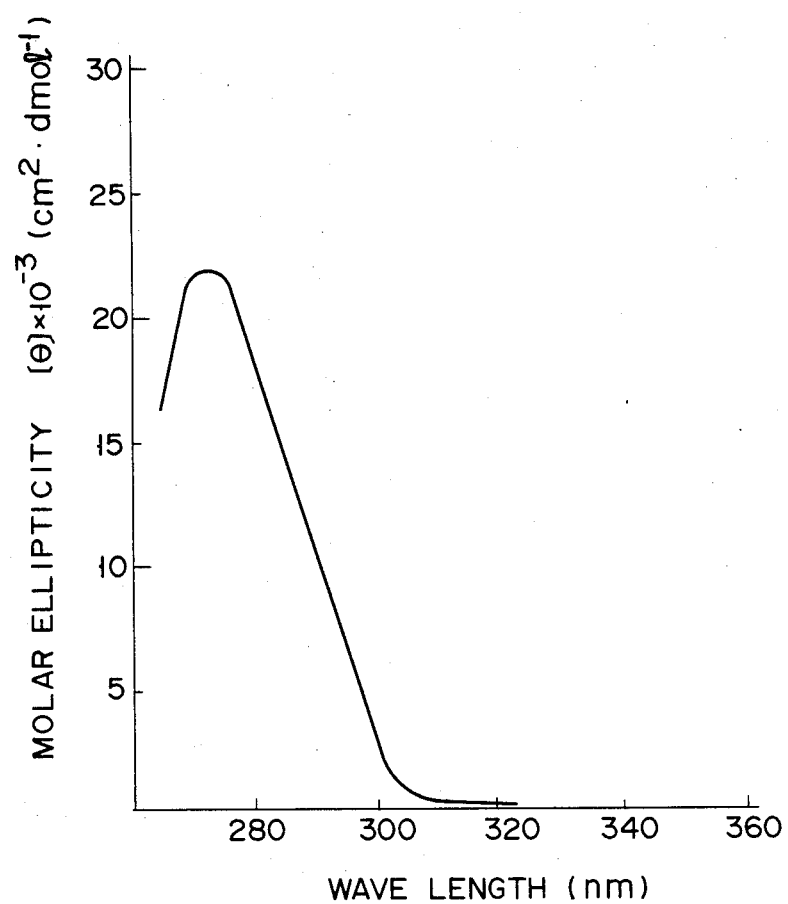
FIG. 2 shows a circular dichroism spectrum, obtained by analyzing the anticancer substance with an optical rotatory dispersion spectrophotometer.

FIG. 2 shows a CD spectrum having a positive peak ($2.2 \times 10^{-4}$) at a wave length of 275 nm. The positive CD band attributes to the existence of tyrosine, tryptophan and S—S bond.

The cancerocidal effect of the substance thus obtained was substantiated as follows:

Experiment 1 (Determination of Cancerocidal Effect by soft agar cloning analysis method)

According to the conventional method (soft agar cloning analysis method), an established cell line of leukocyte of a mouse suffering from lymphocytic leukemia (L-1210/V/C) was innoculated ($5 \times 10^4$ cells) to a medium in which the substance was added.

The 50% growth inhibition concentration (IC$_{50}$) was 1 μg/ml.

Experiment 2 (Test using P-388)

$10^6$ leukocytes from a mouse suffering from lymphocytic leukemia (P-388) were intraperitoneally administered to each of the CDF$_1$ mice of 5 weeks old (10 animals per group). From 24 hours after the administration, the substance was intraperitoneally administered in the amount of 8 mg/kg every day (once a day) for 5 days. In accordance with the conventional method, ratio of surviving days (the ratio of the surviving days of the tested animals and control animals which did not receive the substance) was calculated. The ratio of surviving days (T/C) was 150%.

Experiment 3 (Acute Toxicity Test)

The oral acute toxicity of the anticancer agent of the present invention was determined using DDY mice of 6 weeks old (body weight of 20±1 g, male) and Wister rats (body weight of 200 to 220 g, female). One gram of Chlorella-extracted anticancer agent of the present invention (powdered form) was dissolved in 4 ml of water, and 0.2 ml and 0.5 ml aliquots thereof were administered to 12 mice, respectively using an oral sound. Five milliliters of the same solution was orally administered to each of 10 rats. The animals were raised at 22° to 24° C. in an incubator. Survival of the animals was checked at 24 hours, 72 hours, and 1 week after the administration.

The result was that no animals died. On day 8, the animals were sacrificed and anatomized. Gross examination did not find any abnormality.

If the dose of the anticancer agent is increased, the animals may die because of overeating, so that the maximum limit of the dose is assumed to be 0.5 ml for a mouse of 20 g body weight.

Experiments have proved that the anticancer agent of the present invention can be administered through any route including oral, subcutaneous, intravenous and topical route.

The anticancer agent of the present invention may be suitably administered in the form of, for example, powder, granule, tablet, capsule, injection solution, and topical formulation, by admixing the agent with a pharmaceutically acceptable carrier (vehicle such as lactose and starch; solvent such as olive oil, soybean oil) and formulating it according to a conventional method.

The dose to be administered varies depending on the condition of the patient and on the administration route, but normally 1 mg to 400 mg per 1 kg of body weight for human adult. The dose may be divided into several doses.

What is claimed is:

1. An anticancer agent which is a glycoprotein extraced and isolated from Chlorella, which has an average molecular weight of $4.5 \times 10^4$, of which protein moiety consists of α-helix and random coil, of which sugar moiety consists of β-pollysaccharide, and of wich circular dichroism spectrum has a positive peak at 275 nm.

2. An anticancer agent according to claim 1 for oral, subcutaneous, intravenous or topical administration.

3. An anticancer agent according to claim 1 in powdered, granular, tablet, capsule, injectionsolution or topical formulation form.

4. An anticancer agent according to claim 1 wherein the agent is administered at a dose of 1 mg to 400 mg per 1 kg of body weight for a human adult.

5. An anticancer composition comprising an anticancer effective amount of a substance which is a glycoprotein extracted and isolated form Chlorella, which has an average molecular weight of $4.5 \times 10^4$, of which protein moiety consists of α- helix and random coil, of which sugar moiety consists of β-polysaccharide, and of which circular dichroism spectrum has a positive peak at 275 nm, and a pharmaceutically acceptable carrier.

* * * * *